(12) United States Patent
von Borstel

(10) Patent No.: US 7,582,619 B2
(45) Date of Patent: *Sep. 1, 2009

(54) COMPOSITIONS AND METHODS FOR TREATMENT OF MITOCHONDRIAL DISEASES

(75) Inventor: Reid W. von Borstel, Potomac, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 25 days.

This patent is subject to a terminal disclaimer.

(21) Appl. No.: 11/520,811

(22) Filed: Sep. 14, 2006

(65) Prior Publication Data

US 2007/0010479 A1 Jan. 11, 2007

Related U.S. Application Data

(60) Continuation of application No. 11/127,171, filed on May 12, 2005, now abandoned, which is a division of application No. 09/838,136, filed on Apr. 20, 2001, now Pat. No. 6,956,028, which is a continuation of application No. 09/144,096, filed on Aug. 31, 1998, now Pat. No. 6,472,378.

(51) Int. Cl.
*A61K 48/00* (2006.01)
(52) U.S. Cl. ............................ 514/49; 514/44; 514/50; 536/28.4
(58) Field of Classification Search ........................ None
See application file for complete search history.

(56) References Cited

U.S. PATENT DOCUMENTS

| | | | |
|---|---|---|---|
| 4,960,759 A | 10/1990 | De Luca et al. | |
| 5,470,838 A | 11/1995 | von Borstel et al. | 514/50 |
| 5,736,531 A | 4/1998 | von Borstel et al. | 514/50 |
| 5,968,914 A | 10/1999 | von Borstel et al. | |
| 5,981,601 A | 11/1999 | Nagley et al. | |
| 6,258,795 B1 | 7/2001 | von Borstel et al. | |
| 6,316,426 B1 * | 11/2001 | von Borstel et al. | 514/50 |
| 2002/0028787 A1 | 3/2002 | Watkins et al. | |
| 2004/0224920 A1 | 11/2004 | Naviaux | |
| 2005/0123922 A1 * | 6/2005 | Cattaneo et al. | 435/6 |

FOREIGN PATENT DOCUMENTS

| | | | |
|---|---|---|---|
| WO | WO 96/06640 | * | 3/1996 |
| WO | WO 00/06174 | | 2/2000 |
| WO | WO 00/50043 | | 8/2000 |

OTHER PUBLICATIONS

Bren "Alzheimer's: Searching for a Cure" FDA Consumer Magazine, Jul.-Aug. 2003 Issue, Pub. No. FDA 04-1318C rev.*
Hollander et al. Am. J. Psychiatry (1999), vol. 156:2, pp. 317-320.*
Page et al. Proc. Natl. Acad. Sci. USA (1997), vol. 94, pp. 11601-11606.*
U.S. Appl. No. 60/121,588, filed Feb. 23, 1999, Naviaux, Robert K. Pending U.S. Appl. No. 09/889,251, Naviaux.
The Merck Manual; pp. 1221-126 (1987).
Wardell, T.M., et al; "Changes in the human mitochondrial genome after treatment of malignant disease"; *Muat Res.*; 9;525(1-2):19-27 (Apr. 2003) (Abstract).
Sign, G., et al; "Mitochondrial DNA damage by anticancer agents"; *Pharmal Ther.*; 54(2):217-30 (1992) (Abstract).
Brady, H.R., et al; "Mitochondrial injury: an early event in cisplatin toxicity to renal proximal tubules"; *Am.J. Physiol.*; vol. 258(5 Pt 2):F1181-7 (May 1990) (Abstract).
Branda, R.F., et al; "Dietary modulation of mitochondrial DNA deletions and copy number after chemotherapy in rats"; *Mutat REs.*; 25;501(1-2):29-36 (Apr. 2000) (Abstract).
Solem, L.E., et al; "Disruption of mitochondrial calcium homeostasis following chronic doxorubicin administration"; *Toxicol Appl Pharmacol.*; 129(2):214-22 (Dec. 1994) (Abstract).
Khaidakov, M., et al; "Molecular analysis of mitochondrial DNA mutations from bleomycin-treated rats"; *Mut Res.*; 20;500(1-2):1-8 (Mar. 2002) (Abstract).
Pritsos, C.A. et al; "A new cellular target for mitomycin C: a case for mitochondrial DNA"; *Oncol Res.*; 9(6-7):333-7 (1997) (Abstract).
Chen et al; "Effect of Anti-Human Immunodeficiency Virus Nucleoside Analogs on Mitochondrial DNA and Its Implication for Delayed Toxicity"; Molec. Pharmacol; 39:625-628; (1991).
Keilbaugh et al; "Anti-Human Immunodeficiency Virus Type 1 Therapy and Peripheral Neuropathy: Prevention of 2',3'-Dideoxycytidine Toxicity in PC12 Cells, a Neuronal Model, by Uridine and Pyruvate"; Molec. Pharmacol. 44:702-706 (1993).
Current Claims 1-50; von Borstel et al; U.S. Appl. No. 09/930,494, filed Aug. 16, 2001; (Attorney Reference 1331-352).
Current Claims 1-47; Von Borstel; U.S. Appl. No. 09/763,955, filed Feb. 28, 2001; Attorney Reference 1331-334.
First Amended Cross-Complaint of Defendants The Regents of the University of California and Dr. Robert K. Naviaux; Jul. 26, 2002; pp. 1-18.
Second Amended Complaint of Plaintiff Wellstat Therapeutics Corporation (f/k/a/ Pro-Neuron, Inc.); Aug. 21, 2002; pp. 1-30 and Exhibits A-I.
Letter dated Jul. 27, 1998 from Robert K. Naviaux to the U.S. Food and Drug Administration (FDA).
Dec. 9, 2001 Declaration of Robert Naviaux, M.D. in Support of Defendant The Regents of the University of California's Opposition to Plaintiff Pro-Neuron Inc.'s Application for Temporary Restraining Order and Order to Show Cause.
Tapes (2) of Mitochondrial Dysfunction in Human Pathology conference, Monday, Sep. 7, 1998 afternoon session, Melbourne, Australia, particularly Dr. Naviaux's presentation, second tape, side A.
Dec. 28, 2001 Declaration of William L. Nyhan, M.D., Ph.D. in Support of Defendant The Regents of the University of California's Opposition to Plaintiff Pro-Neuron Inc.'s Motion for Preliminary Injunction.
Naviaux et al, "Clinical experience with uridine and triacetyluridine (PN401) therapy of mitochondrial disease," abstract in meeting program for Mitochondrial Dysfunction in Human Pathology, Sep. 5-7, 1998, Hotel Sofitel, Melbourne, Australia.

(Continued)

*Primary Examiner*—Patrick T Lewis
(74) *Attorney, Agent, or Firm*—Nixon & Vanderhye

(57) ABSTRACT

Compounds, compositions, and methods are provided for treatment of disorders related to mitochondrial dysfunction. The methods comprise administering to a mammal a composition containing pyrimidine nucleotide precursors in amounts sufficient to treat symptoms resulting from mitochondrial respiratory chain deficiencies.

4 Claims, No Drawings

OTHER PUBLICATIONS

Morais, R., and Guertin, D., *Can. J. Biochem.*, vol. 60, p. 290-294, 1982 "On the contribution of the mitochondrial genome to the growth of Chinese hamster embryo cells in culture".

Morias, R., et al, *In Vitro Cellular & Development Biology*, vol. 24, No. 7, Jul. 1988, p. 649-658, "Development and Characterization of Continuous Avian Cell Lines" Depleted of Mitochondrial DNA.

Bodnar, Andrea G., et al, *Biochem. J.*, (1995) 817-822, "Respiratory-deficient human fibroblasts exhibiting defective mitochondrial DNA replication".

Bourgeron, Thomas, et al, *The Journal of Biological Chemistry*, vol. 268, No. 26, Sep. 15, 1993, pp. 19369-19376. "Fate and expression of the deleted mitochondrial DNA differ between human heteroplasmic skin fibroblast and Epstein-Barr virus-transformed lymphocyte cultures".

Löffler, Monika, et al, *Molecular and Cellular Biochemistry*, 174:125-192, 1997, "Dihydroorotat-ubiquinone oxidoreductase links mitochondria in the biosynthesis of pyrimidine nucleotides".

Page, Theodore, et al, *Proc. Natl. Acad. Sci. USA*, vol. 94, pp. 11601-11606, Oct. 1997, "Developmental disorder associated with increased cellular nucleotidase activity".

Secades et al, "Methods and Findings in Experimental . . . ," 17: Supplement B pp. 1-54, (see p. 38, col 2 through p. 39, col. 1, and 40-43) (1995).

Keilbaugh et al (Mol. Pharm. 44: 702-706, abstract only (1995).

Dykens et al, J. Neurochem. 63:584-591, especially see lines 24-28 of abstract; and pp. .589, col 1, first para (1994).

Bodnar et al, Biochem J. 305: 817-822, see especially abstract, lines 6-10 (1995).

Kralovansky et al, "Cancer Chemotherapy and Pharmacology," 32: 243-248, see abstract, lines 4-7 (1993).

Lipp et al, Biology of the Neonate 33: 62-65 , see entire abstract (1978).

Sartori et al, Alcohol 3:97-100, see first and last sentences of abstract (1986).

Agnati et al, Acta Phys. Scanda, 126: 525-531, see abstract, lines 5-15 (1986).

\* cited by examiner

COMPOSITIONS AND METHODS FOR TREATMENT OF MITOCHONDRIAL DISEASES

This application is a continuation of application Ser. No. 11/127,171, filed May 12, 2005 now abandoned, which is a divisional of application Ser. No. 09/838,136, filed Apr. 20, 2001 now U.S. Pat. No. 6,956,028, which is a continuation of application Ser. No. 09/144,096, filed Aug. 31, 1998 now U.S. Pat. No. 6,472,378, the entire content of which is hereby incorporated by reference in this application.

FIELD OF THE INVENTION

This invention relates generally to compounds and methods for treatment and prevention of diseases, developmental delays, and symptoms related to mitochondrial dysfunction. Pyrimidine nucleotide precursors are administered to a mammal, including a human, for the purpose of compensating for mitochondrial dysfunction and for improving mitochondrial functions.

BACKGROUND OF THE INVENTION

Mitochondria are cellular organelles present in most eukaryotic cells. One of their primary functions is oxidative phosphorylation, a process through which energy derived from metabolism of fuels like glucose or fatty acids is converted to ATP, which is then used to drive various energy-requiring biosynthetic reactions and other metabolic activities. Mitochondria have their own genomes, separate from nuclear DNA, comprising rings of DNA with about 16,000 base pairs in human cells. Each mitochondrion may have multiple copies of its genome, and individual cells may have hundreds of mitochondria.

Mitochondrial dysfunction contributes to various disease states. Some mitochondrial diseases are due to mutations or deletions in the mitochondrial genome. Mitochondria divide and proliferate with a faster turnover rate than their host cells, and their replication is under control of the nuclear genome. If a threshold proportion of mitochondria in a cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved.

A fertilized ovum might contain both normal and genetically defective mitochondria. The segregation of defective mitochondria into different tissues during division of this ovum is a stochastic process, as will be the ratio of defective to normal mitochondria within a given tissue or cell (although there can be positive or negative selection for defective mitochondrial genomes during mitochondrial turnover within cells). Thus, a variety of different pathologic phenotypes can emerge out of a particular point mutation in mitochondrial DNA. Conversely, similar phenotypes can emerge from mutations or deletions affecting different genes within mitochondrial DNA. Clinical symptoms in congenital mitochondrial diseases often manifest in postmitotic tissues with high energy demands like brain, muscle, optic nerve, and myocardium, but other tissues including endocrine glands, liver, gastrointestinal tract, kidney, and hematopoietic tissue are also involved, again depending in part on the segregation of mitochondria during development, and on the dynamics of mitochondrial turnover over time.

In addition to congenital disorders involving inherited defective mitochondria, acquired mitochondrial dysfunction contributes to diseases, particularly neurodegenerative disorders associated with aging like Parkinson's, Alzheimer's, Huntington's Diseases. The incidence of somatic mutations in mitochondrial DNA rises exponentially with age; diminished respiratory chain activity is found universally in aging people. Mitochondrial dysfunction is also implicated in excitotoxic neuronal injury, such as that associated with seizures or ischemia.

Treatment of diseases involving mitochondrial dysfunction has heretofore involved administration of vitamins and cofactors used by particular elements of the mitochondrial respiratory chain. Coenzyme Q (ubiquinone), nicotinamide, riboflavin, carnitine, biotin, and lipoic acid are used in patients with mitochondrial disease, with occasional benefit, especially in disorders directly stemming from primary deficiencies of one of these cofactors. However, while useful in isolated cases, no such metabolic cofactors or vitamins have been shown to have general utility in clinical practice in treating mitochondrial diseases. Similarly, dichloracetic acid (DCA) has been used to treat mitochondrial cytopathies such as MELAS; DCA inhibits lactate formation and is primarily useful in cases of mitochondrial diseases where excessive lactate accumulation itself is contributing to symptoms. However, DCA does not address symptoms related to mitochondrial insufficiency per se and can be toxic to some patients, depending on the underlying molecular defects.

Mitochondrial diseases comprise disorders caused by a huge variety of molecular lesions or defects, with the phenotypic expression of disease further complicated by stochastic distributions of defective mitochondria in different tissues.

Commonly owned U.S. Pat. No. 5,583,117 discloses acylated derivatives of cytidine and uridine. Commonly owned application PCT/US 96/10067 discloses the use of acylated pyrimidine nucleosides to reduce the toxicity of chemotherapeutic and antiviral pyrimidine nucleoside analogs.

OBJECTS OF THE INVENTION

It is an object of the invention to provide compositions and methods for treating disorders or pathophysiology associated with mitochondrial dysfunction or mitochondrial respiratory chain dysfunction in a mammal, including a human.

It is an object of the invention to provide compounds and compositions that improve tissue resistance to mitochondrial dysfunction in vivo.

It is an object of the invention to provide compositions and methods for treatment of mitochondrial diseases.

It is an object of the invention to provide agents which compensate broadly for mitochondrial deficits involving a wide variety of molecular pathologies, since, in many cases, precise diagnosis of molecular lesions in mitochondrial disorders is difficult.

It is an object of the invention to provide a practical treatment for mitochondrial diseases that is beneficial in the case of mitochondrial electron transport chain deficits regardless of the specific molecular defects.

It is an object of the invention to provide not only for the relatively rare congenital diseases related to mitochondrial DNA defects, but also for significant neuromuscular and neurodevelopmental disorders that appear in childhood and for common age-related degenerative diseases like Alzheimer's or Parkinson's Diseases.

It is an object of the invention to provide compositions and methods for treatment and prevention of neurodegenerative and neuromuscular disorders.

It is an object of the invention to provide compositions and methods for treatment and prevention of epilepsy.

It is an object of the invention to provide compositions and methods for treatment and prevention of migraine.

It is an object of the invention to provide compositions and methods for preventing death or dysfunction of postmitotic cells in a mammal, including a human.

It is an object of the invention to provide compositions and methods for treatment of neurodevelopmental delay disorders It is a further object of the invention to provide a composition for treatment or prevention of tissue damage due to hypoxia or ischemia.

It is a further object of this invention to provide compositions and methods for treating or preventing ovarian dysfunction, menopause, or secondary consequences of menopause.

It is a further object of the invention to provide compositions and methods for reducing side effects of cancer chemotherapies due to chemotherapy-induced mitochondrial injury.

It is a further object of the invention to provide a method for diagnosing mitochondrial disease and dysfunction.

SUMMARY OF THE INVENTION

The subject invention provides a method for treating pathophysiological consequences of mitochondrial respiratory chain deficiency in a mammal comprising administering to such a mammal in need of such treatment an amount of a pyrimidine nucleotide precursor effective in reducing the pathophysiological consequences. Additionally, the invention provides a method of preventing pathophysiological consequences of mitochondrial respiratory chain deficiency comprising administering to a mammal an amount of a pyrimidine nucleotide precursor effective in preventing the pathophysiological consequences.

In mitochondrial disease the compounds and compositions of the invention are useful for attenuating clinical sequelae stemming from respiratory chain deficiencies. Respiratory chain deficiencies underlying mitochondrial disease are caused by various factors including congenital or inherited mutations and deletions in mitochondrial DNA, deficits in nuclear-encoded proteins affecting respiratory chain activity, as well as somatic mutations, elevated intracellular calcium, excitotoxicity, nitric oxide, hypoxia and axonal transport defects.

The subject invention provides compounds, compositions, and methods for preventing or reducing death and dysfunction of postmitotic cells bearing mitochondrial respiratory chain deficits.

The subject invention furthermore provides compounds, compositions, and methods for treating neurodevelopmental delays in language, motor, executive function, cognitive, and neuropsychological social skills.

The subject invention also relates to treatment of disorders and conditions that are herein disclosed as conditions to which mitochondrial defects contribute and which therefore are subject to treatment with compounds, and compositions of the invention. These include side effects of cancer chemotherapy like peripheral neuropathies, nephropathies, fatigue, and early menopause, as well as ovulatory abnormalities and normal menopause itself.

The subject invention also relates to a method for diagnosing mitochondrial diseases by treating patients with a pyrimidine nucleotide precursor and assessing clinical benefit in selected signs and symptoms.

The invention, as well as other objects, features and advantages thereof will be understood more clearly and fully from the following detailed description, when read with reference to the accompanying results of the experiments discussed in the examples below.

DETAILED DESCRIPTION OF THE INVENTION

The subject invention is related to compounds, compositions, and methods for treating or preventing a variety of clinical disorders secondary to mitochondrial dysfunction, especially deficits in the activity of components of the mitochondrial respiratory chain. Such disorders include congenital mitochondrial cytopathies, neurodevelopmental delays, age-related neurodegenerative diseases, as well as particular diseases affecting the heart, peripheral and autonomic nerves, skeletal muscle, pancreas and other tissues and organs.

A. Definitions

"Mitochondrial disease" refers to disorders to which deficits in mitochondrial respiratory chain activity contribute in the development of pathophysiology of such disorders in a mammal. This category includes 1) congenital genetic deficiencies in activity of one or more components of the mitochondrial respiratory chain; 2) acquired deficiencies in the activity of one or more components of the mitochondrial respiratory chain, wherein such deficiencies are caused by, inter alia, a) oxidative damage during aging; b) elevated intracellular calcium; c) exposure of affected cells to nitric oxide; d) hypoxia or ischemia; or e) microtubule-associated deficits in axonal transport of mitochondria.

The mitochondrial respiratory chain (also known as the electron transport chain) comprises 5 major complexes:

| | |
|---|---|
| Complex I | NADH: ubiquinone reductase |
| Complex II | Succinate: ubiquinone reductase |
| Complex III | ubiquinol: cytochrome-c reductase |
| Complex IV | cytochrome-c oxidase |
| Complex V | ATP synthase |

Complexes I and II accomplish the transfer of electrons from metabolic fuels like glycolysis products and fatty acids to ubiquinone (Coenzyme Q), converting it to ubiquinol. Ubiquinol is converted back to ubiquinone by transfer of electrons to cytochrome c in Complex III. Cytochrome c is reoxidized at Complex IV by transfer of electrons to molecular oxygen, producing water. Complex V utilizes potential energy from the proton gradient produced across the mitochondrial membrane by these electron transfers into ATP.

Dihydro-orotate dehydrogenase (DHODH), is an enzyme involved in de novo synthesis of uridine nucleotides. DHODH activity is coupled to the respiratory chain via transfer of electrons from dihydro-orotate to ubiquinone; these electrons are then passed on to cytochrome c and oxygen via Complexes III and IV respectively. Only Complexes III and IV are directly involved in pyrimidine biosynthesis. Orotate produced by the action of DHODH is converted to uridine monophosphate by phosphoribosylation and decarboxylation.

"Pyrimidine nucleotide precursors" in the context of the invention are intermediates in either the de novo or salvage pathways of pyrimidine nucleotide synthesis that enter into pyrimidine synthesis either distal to DHODH (e.g. orotate) or which do not require DHODH activity for conversion to pyrimidine nucleotides (e.g. cytidine, uridine, or acyl derivatives of cytidine or uridine). Also included within the scope of the invention are pyrimidine nucleoside phosphates (e.g. nucleotides, cytidine diphosphocholine, uridine diphosphoglucose); these compounds are degraded to the level of uridine or cytidine prior to entry into cells and anabolism. Acyl derivatives of cytidine and uridine have better oral bioavailability than the parent nucleosides or nucleotides. Orotic acid and esters thereof are converted to uridine nucleotides and are also useful for accomplishing the goals of the invention.

B. Compounds of the Invention

A primary feature of the present invention is the unexpected discovery that administration of pyrimidine nucleotide precursors is effective in treatment of a large variety of symptoms and disease states related to mitochondrial dysfunction.

Tissue pyrimidine nucleotide levels are increased by administration of any of several precursors. Uridine and cytidine are incorporated into cellular nucleotide pools by phosphorylation at the 5' position; cytidine and uridine nucleotides are interconvertible through enzymatic amination and de-amination reactions. Orotic acid is a key intermediate in de novo biosynthesis of pyrimidine nucleotides. Incorporation of orotic acid into nucleotide pools requires cellular phosphoribosyl pyrophosphate (PRPP). Alternatively (or in addition to provision of exogenous nucleotide precursors), availability of uridine to tissues is increased by administration of compounds which inhibit uridine phosphorylase, the first enzyme in the pathway for degradation of uridine. The compounds of the invention useful in treating mitochondrial diseases and related disorders include uridine, cytidine, orotate, orally bioavailable acyl derivatives or esters of these pyrimidine nucleotide precursors, and inhibitors of the enzyme uridine phosphorylase.

In reference to acyl derivatives of cytidine and uridine, the following definitions pertain:

The term "acyl derivative" as used herein means a derivative of a pyrimidine nucleoside in which a substantially non-toxic organic acyl substituent derived from a carboxylic acid is attached to one or more of the free hydroxyl groups of the ribose moiety of the oxypurine nucleoside with an ester linkage and/or where such a substituent is attached to the amine substituent on the purine ring of cytidine, with an amide linkage. Such acyl substituents are derived from carboxylic acids which include, but are not limited to, compounds selected from the group consisting of a fatty acid, an amino acid, nicotinic acid, dicarboxylic acids, lactic acid, p-aminobenzoic acid and orotic acid. Advantageous acyl substituents are compounds which are normally present in the body, either as dietary constituents or as intermediary metabolites.

The term "pharmaceutically acceptable salts" as used herein means salts with pharmaceutically acceptable acid or base addition salts of the derivatives, which include, but are not limited to, sulfuric, hydrochloric, or phosphoric acids, or, in the case of orotate, sodium or calcium hydroxides, and cationic amino acids, especially lysine.

The term "amino acids" as used herein includes, but is not limited to, glycine, the L forms of alanine, valine, leucine, isoleucine, phenylalanine, tyrosine, proline, hydroxyproline, serine, threonine, cysteine, cystine, methionine, tryptophan, aspartic acid, glutamic acid, arginine, lysine, histidine, ornithine, hydroxylysine, carnitine, and other naturally occurring amino acids.

The term "fatty acids" as used herein means aliphatic carboxylic acids having 2-22 carbon atoms. Such fatty acids may be saturated, partially saturated or polyunsaturated.

The term "dicarboxylic acids" as used herein means fatty acids with a second carboxylic acid substituent.

Compounds of the invention have the following structures:

In all cases except where indicated, letters and letters with subscripts symbolizing variable substituents in the chemical structures of the compounds of the invention are applicable only to the structure immediately preceding the description of the symbol.

(1) An acyl derivative of uridine having the formula:

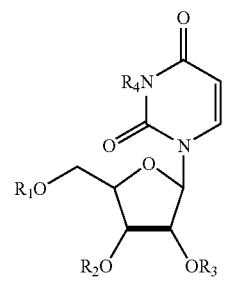

wherein $R_1$, $R_2$, $R_3$ and $R_4$ are the same or different and each is hydrogen or an acyl radical of a metabolite, provided that at least one of said R substituents is not hydrogen, or a pharmaceutically acceptable salt thereof.

(2) An acyl derivative of cytidine having the formula:

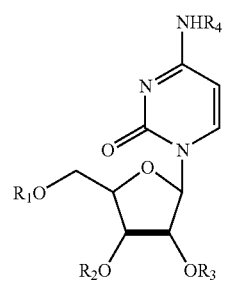

wherein $R_1$, $R_2$, $R_3$ and $R_4$ are the same or different and each is hydrogen or an acyl radical of a metabolite, provided that at least one of said R substituents is not hydrogen, or a pharmaceutically acceptable salt thereof.

The compounds of the invention useful in treating mitochondrial diseases include:

(3) An acyl derivative of uridine having the formula:

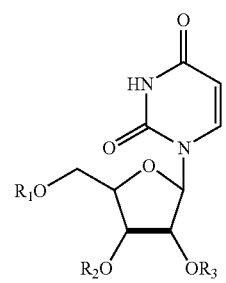

wherein $R_1$, $R_2$, and $R_3$ are the same, or different, and each is hydrogen or an acyl radical of a. an unbranched fatty acid with 2 to 22 carbon atoms, b. an amino acid selected from the group consisting of glycine, the L forms of alanine, valine, leucine, isoleucine, tyrosine, proline, hydroxyproline, serine, threonine, cystine, cysteine, aspartic acid, glutamic acid, arginine, lysine, histidine, carnitine and ornithine, c. a dicarboxylic acid having 3-22 carbon atoms, d. a carboxylic acid selected from one or more of the group consisting of glycolic acid, pyruvic acid, lactic acid, enolpyruvic acid, lipoic acid, pantothenic acid, acetoacetic acid, p-aminobenzoic acid, betahydroxybutyric acid, orotic acid, and creatine.

(4) An acyl derivatives of cytidine having the formula:

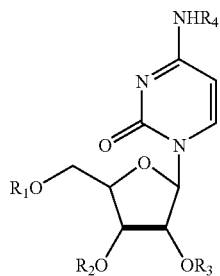

wherein $R_1$, $R_2$, $R_3$, and $R_4$ are the same, or different, and each is hydrogen or an acyl radical of a. an unbranched fatty acid with 2 to 22 carbon atoms, b. an amino acid selected from the group consisting of glycine, the L forms of phenylalanine, alanine, valine, leucine, isoleucine, tyrosine, proline, hydroxyproline, serine, threonine, cystine, cysteine, aspartic acid, glutamic acid, arginine, lysine, histidine carnitine and ornithine, c. a dicarboxylic acid having 3-22 carbon atoms, d. a carboxylic acid selected from one or more of the group consisting of glycolic acid, pyruvic acid, lactic acid, enolpyruvic acid, lipoic acid, pantothenic acid, acetoacetic acid, p-aminobenzoic acid, betahydroxybutyric acid, orotic acid, and creatine.

(5) An acyl derivative of uridine having the formula:

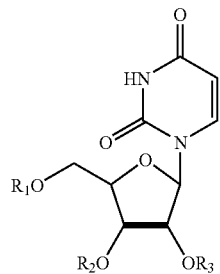

wherein at least one of $R_1$, $R_2$, or $R_3$ is a hydrocarbyloxycarbonyl moiety containing 2-26 carbon atoms and the remaining R substituents are independently a hydrocarbyloxycarbonyl or hydrocarbylcarbonyl moiety or H or phosphate.

(6) An acyl derivative of cytidine having the formula:

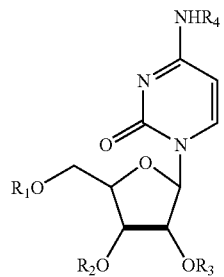

wherein at least one of $R_1$, $R_2$, $R_3$ or $R_4$ is a hydrocarbyloxycarbonyl moiety containing 2-26 carbon atoms and the remaining R substituents are independently a hydrocarbyloxycarbonyl or hydrocarbylcarbonyl moiety or H or phosphate.

(7) Orotic acid or salts thereof:

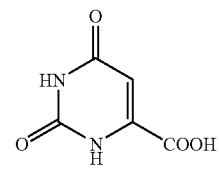

Pharmaceutically-acceptable salts of orotic acid include those in which the cationic component of the salt is sodium, potassium, a basic amino acid such as arginine or lysine, methylglucamine, choline, or any other substantially non-toxic water soluble cation with a molecular weight less than about 1000 daltons.

8) Alcohol-substituted orotate derivatives:

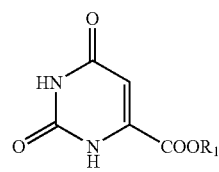

wherein $R_1$ is a radical of an alcohol containing 1 to 20 carbon atoms joined to orotate via an ester linkage.

Also encompassed by the invention are the pharmaceutically acceptable salts of the above-noted compounds.

Advantageous compounds of the invention are short-chain (2 to 6 carbon atoms) fatty acid esters of uridine or cytidine. Particularly advantageous compounds are triacetyluridine or triacetylcytidine. Such compounds have better oral bioavailabilty than the parent nucleosides, and are rapidly deacetylated following absorption after oral administration.

Pyruvic acid is useful for treatment of cells with defective mitochondrial function. Cells with reduced capability for mitochondrial oxidative phosphorylation must rely on glycolysis for generation of ATP. Glycolysis is regulated by the redox state of cells. Specifically, NAD+ is required for optimal glucose flux, producing NADH in the process. In order to maximize energy production from glycolysis, NADH must be reoxidized to NAD+. Exogenous pyruvate can reoxidize NADH, in part via a plasma membrane enzyme, NADH Oxidase.

Uridine tripyruvate (2',3',5'-tri-O-pyruvyluridine) provides the benefits of both pyrimidines and pyruvate, delivering both with a single chemical entity, and avoiding the load of sodium, calcium, or other cations in the corresponding salts of pyruvic acid.

Inhibitors of Uridine Phosphorylase

An alternative or complementary strategy for treating mitochondrial diseases involves inhibition of uridine catabolism with an inhibitor of the enzyme uridine phosphorylase.

Examples of inhibitors of uridine phosphorylase that are useful for treatment of mitochondrial disease include but are not limited to 5-benzyl barbiturate or 5-benzylidene barbiturate derivatives including 5-benzyl barbiturate, 5-benzyloxybenzyl barbiturate, 5-benzyloxybenzyl-1-[(1-hydroxy-2-ethoxy)methyl] barbiturate, 5-benzyloxybenzylacetyl-1-[(1-hydroxy-2-ethoxy)methyl] barbiturate, and 5-methoxybenzylacetylacyclobarbiturate, 2,2'-anhydro-5-ethyluridine, 5-ethyl-2-deoxyuridine and acyclouridine compounds, particularly 5-benzyl substituted acyclouridine congeners including but not limited to benzylacyclouridine, benzyloxybenzylacyclouridine, aminomethyl-benzylacyclouridine, aminomethylbenzyloxy-benzylacyclouridine, hydroxymethyl-benzylacyclouridine, and hydroxymethylbenzyloxy-benzylacyclouridine. See also WO 89/09603 and WO 91/16315, hereby incorporated by reference.

C. Compositions of the Invention

In one embodiment of the invention, novel pharmaceutical compositions comprise as an active agent one or more pyrimidine nucleotide precursors selected from the group consisting of uridine, cytidine, orotic acid or its salts or esters, and acyl derivatives of these pyrimidine nucleotide precursors, together with a pharmaceutically acceptable carrier.

The compositions, depending on the intended use and route of administration, are manufactured in the form of a liquid, a suspension, a tablet, a capsule, a dragee, an injectable solution, or a suppository (see discussion of formulation below).

In another embodiment of the invention, the composition comprises at least one pyrimidine nucleotide precursor and an agent which inhibits the degradation of uridine, such as an inhibitor of the enzyme uridine phosphorylase. Examples of inhibitors of uridine phosphorylase include but are not limited to 5-benzyl barbiturate or 5-benzylidene barbiturate derivatives including 5-benzyl barbiturate, 5-benzyloxybenzyl barbiturate, 5-benzyloxybenzyl-1-[(1-hydroxy-2-ethoxy)methyl] barbiturate, 5-benzyloxybenzylacetyl-1-[(1-hydroxy-2-ethoxy)methyl] barbiturate, and 5-methoxybenzylacetylacyclobarbiturate, 2,2'-anhydro-5-ethyluridine, and acyclouridine compounds, particularly 5-benzyl substituted acyclouridine congeners including but not limited to benzylacyclouridine, benzyloxybenzyl-acyclouridine, aminomethyl-benzylacyclouridine, aminomethyl-benzyloxybenzylacyclouridine, hydroxymethyl-benzylacyclouridine, and hydroxymethylbenzyloxybenzylacyclouridine. Furthermore, it is within the scope of the invention to utilize an inhibitor of uridine phosphorylase alone, without coadministration of a pyrimidine nucleotide precursor, for the purpose of treating mitochondrial diseases or pathophysiologies associated with mitochondrial respiratory chain dysfunction.

Further embodiments of the invention comprise a pyrimidine nucleotide precursor combined with one or more other agents with protective or supportive activity relative to mitochondrial structure and function. Such agents, presented with recommended daily doses in mitochondrial diseases include, but are not limited to, pyruvate (1 to 10 grams/day). Coenzyme Q (1 to 4 mg/kg/day), alanine (1-10 grams/day), lipoic acid (1 to 10 mg/kg/day), carnitine (10 to 100 mg/kg/day), riboflavin (20 to 100 mg/day, biotin (1 to 10 mg/day), nicotinamide (20 to 100 mg/day), niacin (20 to 100 mg/day), Vitamin C (100 to 1000 mg/day), Vitamin E (200-400 mg/day), and dichloroacetic acid or its salts. In the case of pyruvate, this active agent can be administered as pyruvic acid, pharmaceutically acceptable salts thereof, or pyruvic acid esters having an alcohol moiety containing 2 to 10 carbon atoms.

D. Therapeutic Uses of the Compounds and Compositions of the Invention

Diseases related to mitochondrial respiratory chain dysfunction can be divided into several categories based on the origin of mitochondrial defects.

Congenital mitochondrial diseases are those related to hereditary mutations, deletions, or other defects in mitochondrial DNA or in nuclear genes regulating mitochondrial DNA integrity, or in nuclear genes encoding proteins that are critical for mitochondrial respiratory chain function.

Acquired mitochondrial defects comprise primarily 1) damage to mitochondrial DNA due to oxidative processes or aging; 2) mitochondrial dysfunction due to excessive intracellular and intramitochondrial calcium accumulation; 3) inhibition of respiratory chain complexes with endogenous or exogenous respiratory chain inhibitors; 4) acute or chronic oxygen deficiency; and 5) impaired nuclear-mitochondrial interactions, e.g. impaired shuttling of mitochondria in long axons due to microtubule defects.

The most fundamental mechanisms involved in acquired mitochondrial defects, and which underlie pathogenesis of a variety of forms of organ and tissue dysfunction, include:

Calcium accumulation: A fundamental mechanism of cell injury, especially in excitable tissues, involves excessive calcium entry into cells, as a result of either leakage through the plasma membrane or defects in intracellular calcium handling mechanisms. Mitochondria are major sites of calcium sequestration, and preferentially utilize energy from the respiratory chain for taking up calcium rather than for ATP synthesis, which results in a downward spiral of mitochondrial failure, since calcium uptake into mitochondria results in diminished capabilities for energy transduction.

Excitotoxicity: Excessive stimulation of neurons with excitatory amino acids is a common mechanism of cell death or injury in the central nervous system. Activation of glutamate receptors, especially of the subtype designated NMDA receptors, results in mitochondrial dysfunction, in part through elevation of intracellular calcium during excitotoxic stimulation. Conversely, deficits in mitochondrial respiration and oxidative phosphorylation sensitizes cells to excitotoxic stimuli, resulting in cell death or injury during exposure to levels of excitotoxic neurotransmitters or toxins that would be innocuous to normal cells.

Nitric oxide exposure: Nitric oxide (−1 micromolar) inhibits cytochrome oxidase (Complex IV) and thereby inhibits mitochondrial respiration (Brown G C, Mol. Cell. Biochem. 174: 189-192, 1997); moreover, prolonged exposure to NO irreversibly reduces Complex I activity. Physiological or pathophysiological concentrations of NO thereby inhibit pyrimidine biosynthesis. Nitric oxide is implicated in a variety of neurodegenerative disorders, and is involved in mediation of excitotoxic and post-hypoxic damage to neurons.

Hypoxia: Oxygen is the terminal electron acceptor in the respiratory chain. Oxygen deficiency impairs electron transport chain activity, resulting in diminished pyrimidine synthesis as well as diminished ATP synthesis via oxidative phosphorylation. Human cells proliferate and retain viability under virtually anaerobic conditions if provided with uridine and pyruvate (or a similarly effective agent for oxidizing NADH to optimize glycolytic ATP production).

Nuclear-mitochondrial interactions: Transcription of mitochondrial DNA encoding respiratory chain components requires nuclear factors. In neuronal axons, mitochondria must shuttle back and forth to the nucleus in order to maintain respiratory chain activity. If axonal transport is impaired by hypoxia or by drugs like taxol which affect microtubule stability, mitochondria distant from the nucleus undergo loss of cytochrome oxidase activity.

In the nervous system especially, mitochondrial respiratory chain deficits have two generalizable consequences: 1) Delayed or aberrant development of neuronal circuits within the nervous system; and 2) accelerated degeneration of neurons and neural circuits, either acutely or over a period of years, depending on the severity of the mitochondrial deficits and other precipitating factors. Analogous patterns of impaired development and accelerated degeneration pertain to non-neural tissues and systems as well.

Mitochondrial Dysfunction and Pyrimidine Biosynthesis

Cells with severely damaged mitochondria (including total deletion of mitochondrial DNA, with a consequent shutdown of respiratory chain activity) can survive in culture if provided with two agents which compensate for critical mitochondrial functions: uridine and pyruvate. Uridine is required in vitro because a limiting enzyme for de novo synthesis of uridine nucleotides, dihydro-orotate dehydrogenase (DHODH), is coupled to the mitochondrial respiratory chain, via ubiquinone as a proximal electron acceptor, cytochrome c as an intermediate, and oxygen as a terminal electron acceptor (Loffler et al., Mol. Cell. Biochem. 174:125-129, 1997). DHODH is required for synthesis of orotate, which is then phosphoribosylated and decarboxylated to produce uridine monophosphate (UMP). All other pyrimidines in cells are derived from UMP. Cells from patients with mitochondrial disease due to defects in mitochondrial DNA require exogenous uridine in order to survive outside of the milieu of the body, wherein pyrimidines, derived from other cells or the diet, and transported via the circulation, are prima facie sufficient to support their viability (Bourgeron, et al. Neuromusc. Disord. 3:605-608, 1993). Significantly, intentional inhibition of DHODH with drugs like Brequinar or Leflunomide results in dose-limiting cytotoxic damage to the hematopoietic system and gastrointestinal mucosa, in contrast to the predominant involvement of postmitotic tissues like the nervous system and muscle in clinical mitochondrial disease.

An important feature of the subject invention is the unexpected result that treatment of patients with mitochondrial disease caused by a variety of underlying molecular defects results in clinical improvement in a diverse assortment of symptoms in vivo in patients (Examples 1-4). It is significant and further unexpected that clinical benefit has been observed in patients with no detectable defects in the respiratory chain complexes (III and IV) that are involved in pyrimidine biosynthesis.

Treatment of Congenital Mitochondrial Cytopathies

Mitochondrial DNA Defects

A number of clinical syndromes have been linked to mutations or deletions in mitochondrial DNA. Mitochondrial DNA is inherited maternally, with virtually all of the mitochondria in the body derived from those provided by the oocyte. If there is a mixture of defective and normal mitochondria in an oocyte, the distribution and segregation of mitochondria is a stochastic process. Thus, mitochondrial diseases are often multisystem disorders, and a particular point mutation in mitochondrial DNA, for example, can result in dissimilar sets of signs and symptoms in different patients. Conversely, mutations in two different genes in mitochondrial DNA can result in similar symptom complexes.

Nonetheless, some consistent symptom patterns have emerged in conjunction with identified mitochondrial DNA defects, and these comprise the classic "mitochondrial diseases", some of which are listed immediately below. Nonetheless, an important aspect of the subject invention is the recognition that the concept of mitochondrial disease and its treatment with compounds and compositions of the invention extends to many other disease conditions which are also disclosed herein.

Some of the major mitochondrial diseases associated with mutations or deletions of mitochondrial DNA include:

MELAS: (Mitochondrial Encephalomyopathy Lactic Acidemia, and Stroke-like episodes.

MERRF: Myoclonic Epilepsy with "Ragged Red" (muscle) Fibers

NARP: Neurogenic muscle weakness, Ataxia and Retinitis Pigmentosa

LHON: Leber's Hereditary Optic Neuropathy

Leigh's Syndrome (Subacute Necrotizing Encephalomyopathy)

PEO: Progressive External Opthalmoplegia

Kearns-Sayres Syndrome (PEO, pigmentary retinopathy, ataxia, and heart-block)

Other common symptoms of mitochondrial diseases which may be present alone or in conjunction with these syndromes include cardiomyopathy, muscle weakness and atrophy, developmental delays (involving motor, language, cognitive or executive function), ataxia, epilepsy, renal tubular acidosis, peripheral neuropathy, optic neuropathy, autonomic neuropathy, neurogenic bowel dysfunction, sensorineural deafness, neurogenic bladder dysfunction, dilating cardiomyopathy, migraine, hepatic failure, lactic acidemia, and diabetes mellitus.

In addition, gene products and tRNA encoded by mitochondrial DNA, many proteins involved in, or affecting, mitochondrial respiration and oxidative phosphorylation are encoded by nuclear DNA. In fact, approximately 3000 proteins, or 20% of all proteins encoded by the nuclear genome, are physically incorporated into, or associated with, mitochondria and mitochondrial functions, although only about 100 are directly involved as structural components of the respiratory chain. Therefore, mitochondrial diseases involve not only gene products of mitochondrial DNA, but also nuclear encoded proteins affecting respiratory chain function.

Metabolic stressors like infections can unmask mitochondrial defects that do not necessarily yield symptoms under normal conditions. Neuromuscular or neurological setbacks during infection are a hallmark of mitochondrial disease. Conversely, mitochondrial respiratory chain dysfunction can render cells vulnerable to stressors that would otherwise be innocuous.

As is demonstrated in the Examples, compounds and compositions of the invention are useful for treatment of a very broad spectrum of signs and symptoms in mitochondrial diseases with different underlying molecular pathologies. The broad applicability of the methods of the invention are unexpected and set the compounds and compositions of the invention apart from other therapies of mitochondrial disease that have been attempted e.g. Coenzyme Q, B vitamins, carnitine, and lipoic acid, which generally address very specific reactions and cofactors involved in mitochondrial function and which are therefore useful only in isolated cases. However, such metabolic interventions with antioxidants and cofactors of respiratory chain complexes are compatible with concurrent treatment with compounds and compositions of the invention, and in fact are used to their best advantage in combination with compounds and compositions of the invention.

Treatment of Neuromuscular Degenerative Disorders

Friedreich's Ataxia

A gene defect underlying Friedreich's Ataxia (FA), the most common hereditary ataxia, was recently identified and is designated "frataxin". In FA, after a period of normal development, deficits in coordination develop which progress to paralysis and death, typically between the ages of 30 and 40. The tissues affected most severely are the spinal cord, peripheral nerves, myocardium, and pancreas. Patients typically lose motor control and are confined to wheel chairs, and are commonly afflicted with heart failure and diabetes.

The genetic basis for FA involves GAA trinucleotide repeats in an intron region of the gene encoding frataxin. The presence of these repeats results in reduced transcription and expression of the gene. Frataxin is involved in regulation of mitochondrial iron content. When cellular frataxin content is subnormal, excess iron accumulates in mitochondria, promoting oxidative damage and consequent mitochondrial degeneration and dysfunction.

When intermediate numbers of GAA repeats are present in the frataxin gene intron, the severe clinical phenotype of ataxia may not develop. However, these intermediate-length trinucleotide extensions are found in 25 to 30% of patients with non-insulin dependent diabetes mellitus, compared to about 5% of the nondiabetic population.

Compounds and compositions of the invention are useful for treating patients with disorders related to deficiencies or defects in frataxin, including Friedreich's Ataxia, myocardial dysfunction, diabetes mellitus and complications of diabetes like peripheral neuropathy. Conversely, diagnostic tests for presumed frataxin deficiencies involving PCR tests for GAA intron repeats are useful for identifying patients who will benefit from treatment with compounds and compositions of the invention.

Muscular Dystrophy

Muscular dystrophy refers to a family of diseases involving deterioration of neuromuscular structure and function, often resulting in atrophy of skeletal muscle and myocardial dysfunction. In the case of Duchenne muscular dystrophy, mutations or deficits in a specific protein, dystrophin, are implicated in its etiology. Mice with their dystrophin genes inactivated display some characteristics of muscular dystrophy, and have an approximately 50% deficit in mitochondrial respiratory chain activity. A final common pathway for neuromuscular degeneration in most cases is calcium-mediated impairment of mitochondrial function. Compounds and compositions of the invention are useful for reducing the rate of decline in muscular functional capacities and for improving muscular functional status in patients with muscular dystrophy.

Multiple Sclerosis

Multiple sclerosis (MS) is a neuromuscular disease characterized by focal inflammatory and autoimmune degeneration of cerebral white matter. Periodic exacerbations or attacks are significantly correlated with upper respiratory tract and other infections, both bacterial and viral, indicating that mitochondrial dysfunction plays a role in MS. Nitric oxide Depression of neuronal mitochondrial respiratory chain activity caused by Nitric Oxide (produced by astrocytes) is implicated as a molecular mechanism contributing to MS.

Compounds and compositions of the invention are useful for treatment of patients with multiple sclerosis, both prophylactically and during episodes of disease exacerbation.

Treatment of Disorders of Neuronal Instability

Treatment of Seizure Disorders

Epilepsy is often present in patients with mitochondrial cytopathies, involving a range of seizure severity and frequency, e.g. absence, tonic, atonic, myoclonic, and status epilepticus, occurring in isolated episodes or many times daily.

In patients with seizures secondary to mitochondrial dysfunction, compounds and methods of the invention are useful for reducing frequency and severity of seizure activity.

Treatment and Prevention of Migraine

Metabolic studies on patients with recurrent migraine headaches indicate that deficits in mitochondrial activity are commonly associated with this disorder, manifesting as impaired oxidative phosphorylation and excess lactate production. Such deficits are not necessarily due to genetic defects in mitochondrial DNA. Migraineurs are hypersensitive to nitric oxide, an endogenous inhibitor of Cytochrome c Oxidase. In addition, patients with mitochondrial cytopathies, e.g. MELAS, often have recurrent migraines.

In patients with recurrent migraine headaches, compounds, compositions, and methods of the invention are useful for prevention and treatment, especially in the case of headaches refractory to ergot compounds or serotonin receptor antagonists.

As demonstrated in Example 1, compounds and compositions of the invention are useful for treatment of migraines associate with mitochondrial dysfunction.

Treatment of Developmental Delay

Delays in neurological or neuropsychological development are often found in children with mitochondrial diseases. Development and remodeling of neural connections requires intensive biosynthetic activity, particularly involving synthesis of neuronal membranes and myelin, both of which require pyrimidine nucleotides as cofactors. Uridine nucleotides are involved in activation and transfer of sugars to glycolipids and glycoproteins. Cytidine nucleotides are derived from uridine nucleotides, and are crucial for synthesis of major membrane phospholipid constituents like phosphatidylcholine, which receives its choline moiety from cytidine diphosphocholine. In the case of mitochondrial dysfunction (due to either mitochondrial DNA defects or any of the acquired or conditional deficits like exicitoxic or nitric oxide-mediated mitochondrial dysfunction described above) or other conditions resulting in impaired pyrimidine synthesis, cell proliferation and axonal extension is impaired at crucial stages in development of neuronal interconnections and circuits, resulting in delayed or arrested development of neuropsychological functions like language, motor, social, executive function, and cognitive skills. In autism for example, magnetic resonance spectroscopy measurements of cerebral phosphate compounds indicates that there is global undersynthesis of membranes and membrane precursors indicated by reduced levels of uridine diphospho-sugars, and cytidine nucleotide derivatives involved in membrane synthesis (Minshew et al., Biological Psychiatry 33:762-773, 1993).

Disorders characterized by developmental delay include Rett's Syndrome, pervasive developmental delay (or PDD-NOS: "pervasive developmental delay—not otherwise specified" to distinguish it from specific subcategories like autism), autism, Asperger's Syndrome, and Attention Deficit/Hyperactivity Disorder (ADHD), which is becoming recognized as a delay or lag in development of neural circuitry underlying executive functions.

Compounds and compositions of the invention are useful for treating patients with neurodevelopmental delays involving motor, language, executive function, and cognitive skills. Current treatments for such conditions, e.g. ADHD, involve amphetamine-like stimulants that enhance neurotransmission in some affected underdeveloped circuits, but such agents, which may improve control of disruptive behaviors, do not improve cognitive function, as they do not address underlying deficits in the structure and interconnectedness of the implicated neural circuits.

Compounds and compositions of the invention are also useful in the case of other delays or arrests of neurological and neuropsychological development in the nervous system and somatic development in non-neural tissues like muscle and endocrine glands.

Treatment of Neurodegenerative Disorders

The two most significant severe neurodegenerative diseases associated with aging, Alzheimer's Disease (AD) and Parkinson's Disease (PD), both involve mitochondrial dysfunction in their pathogenesis. Complex I deficiencies in particular are frequently found not only in the nigrostriatal neurons that degenerate in Parkinson's disease, but also in peripheral tissues and cells like muscle and platelets of Parkinson's Disease patients.

In Alzheimer's Disease, mitochondrial respiratory chain activity is often depressed, especially Complex IV (Cytochrome c Oxidase). Moreover, mitochondrial respiratory function altogether is depressed as a consequence of aging, further amplifying the deleterious sequelae of additional molecular lesions affecting respiratory chain function.

Other factors in addition to primary mitochondrial dysfunction underlie neurodegeneration in AD, PD, and related disorders. Excitotoxic stimulation and nitric oxide are implicated in both diseases, factors which both exacerbate mitochondrial respiratory chain deficits and whose deleterious actions are exaggerated on a background of respiratory chain dysfunction.

Huntington's Disease also involves mitochondrial dysfunction in affected brain regions, with cooperative interactions of excitotoxic stimulation and mitochondrial dysfunction contributing to neuronal degeneration.

Compounds and compositions of the invention are useful for attenuating progression of age-related neurodegenerative disease including AD and PD.

Amyotrophic Lateral Sclerosis

One of the major genetic defects in patients with Amyotrophic Lateral Sclerosis (ALS; Lou Gehrig's Disease; progressive degeneration of motor neurons, skeletal muscle atrophy, inevitably leading to paralysis and death) is mutation or deficiency in Copper-Zinc Superoxide Dismutase (SOD1), an antioxidant enzyme. Mitochondria both produce and are primary targets for reactive oxygen species. Inefficient transfer of electrons to oxygen in mitochondria is the most significant physiological source of free radicals in mammalian systems. Deficiencies in antioxidants or antioxidant enzymes can result in or exacerbate mitochondrial degeneration. Mice transgenic for mutated SOD1 develop symptoms and pathology similar to those in human ALS. The development of the disease in these animals has been shown to involve oxidative destruction of mitochondria followed by functional decline of motor neurons and onset of clinical symptoms (Kong and Xu, J. Neurosci. 18:3241-3250, 1998). Skeletal muscle from ALS patients has low mitochondrial Complex I activity (Wiedemann et al., J. Neurol. Sci 156:65-72, 1998).

Compounds, compositions, and methods of the invention are useful for treatment of ALS, for reversing or slowing the progression of clinical symptoms.

Protection Against Ischemia and Hypoxia

Oxygen deficiency results in both direct inhibition of mitochondrial respiratory chain activity by depriving cells of a terminal electron acceptor for Cytochrome c reoxidation at Complex IV, and indirectly, especially in the nervous system, via secondary post-anoxic excitotoxicity and nitric oxide formation.

In conditions like cerebral anoxia, angina or sickle cell anemia crises, tissues are relatively hypoxic. In such cases, compounds of the invention provide protection of affected tissues from deleterious effects of hypoxia, attenuate secondary delayed cell death, and accelerate recovery from hypoxic tissue stress and injury.

Renal Tubular Acidosis

Acidosis due to renal dysfunction is often observed in patients with mitochondrial disease, whether the underlying respiratory chain dysfunction is congenital or induced by ischemia or cytotoxic agents like cisplatin. Renal tubular acidosis often requires administration of exogenous sodium bicarbonate to maintain blood and tissue pH.

In Example 3, administration of a compound of the invention caused an immediate reversal of renal tubular acidosis in a patient with a severe Complex I deficiency. Compounds and compositions of the invention are useful for treating renal tubular acidosis and other forms of renal dysfunction caused by mitochondrial respiratory chain deficits.

Age-Related Neurodegeneration and Cognitive Decline

During normal aging, there is a progressive decline in mitochondrial respiratory chain function. Beginning about age 40, there is an exponential rise in accumulation of mitochondrial DNA defects in humans, and a concurrent decline in nuclear-regulated elements of mitochondrial respiratory activity.

de Grey (Bioessays, 19:161-167, 1998) discussed mechanisms underlying the observation that many mitochondrial DNA lesions have a selection advantage during mitochondrial turnover, especially in postmitotic cells. The proposed mechanism is that mitochondria with a defective respiratory chain produce less oxidative damage to themselves than do mitochondria with intact functional respiratory chains (mitochondrial respiration is the primary source of free radicals in the body). Therefore, normally-functioning mitochondria accumulate oxidative damage to membrane lipids more rapidly than do defective mitochondria, and are therefore "tagged" for degradation by lysosomes. Since mitochondria within cells have a half life of about 10 days, a selection advantage can result in rapid replacement of functional mitochondria with those with diminished respiratory activity, especially in slowly dividing cells. The net result is that once a mutation in a gene for a mitochondrial protein that reduces oxidative damage to mitochondria occurs, such defective mitochondria will rapidly populate the cell, diminishing or eliminating its respiratory capabilities. The accumulation of such cells results in aging or degenerative disease at the organismal level. This is consistent with the progressive mosaic appearance of cells with defective electron transport activity in muscle, with cells almost devoid of Cytochrome c Oxidase (COX) activity interspersed randomly amidst cells with normal activity, and a higher incidence of COX-negative cells in biopsies from older subjects. The organism, during aging, or in a variety of mitochondrial diseases, is thus faced with a situation in which irreplaceable postmitotic cells (e.g. neurons, skeletal and cardiac muscle) must be preserved and their function maintained to a significant degree, in the face of an inexorable progressive decline in mitochondrial respiratory chain function. Neurons with dysfunctional mitochondria become progressively more sensitive to insults like excitotoxic injury. Mitochondrial failure contributes to most degenerative diseases (especially neurodegeneration) that accompany aging.

Congenital mitochondrial diseases often involve early-onset neurodegeneration similar in fundamental mechanism to disorders that occur during aging of people born with normal mitochondria. The demonstration disclosed in the Examples that compounds and compositions of the invention are useful in treatment of congenital or early-onset mitochondrial disease provides direct support for the utility of compounds and compositions of the invention for treatment of age-related tissue degeneration.

Compounds and compositions of the invention are useful for treating or attenuating cognitive decline and other degenerative consequences of aging.

Mitochondria and Cancer Chemotherapy

Mitochondrial DNA is typically more vulnerable to damage than is nuclear DNA for several reasons:
1. Mitochondrial DNA has a less sophisticated repair system than does nuclear DNA.
2. Virtually all of the mitochondrial DNA strands encode important proteins, so that any defect will potentially affect mitochondrial function. Nuclear DNA contains long regions that do not encode proteins, wherein mutations or damage are essentially inconsequential.
3. Defective mitochondria often have a selection advantage over normal, active ones during proliferation and turnover.
4. Mitochondrial DNA is not protected by histones Empirically, mitochondrial DNA damage is more extensive and persists longer than nuclear DNA damage in cells subjected to oxidative stress or cancer chemotherapy agents like cisplatin due to both greater vulnerability and less efficient repair of mitochondrial DNA. Although mitochondrial DNA may be more sensitive to damage than nuclear DNA, it is relatively resistant, in some situations, to mutagenesis by chemical carcinogens. This is because mitochondria respond to some types of mitochondrial DNA damage by destroying their defective genomes rather than attempting to repair them. This results in global mitochondrial dysfunction for a period after cytotoxic chemotherapy. Clinical use of chemotherapy agents like cisplatin, mitomycin, and cytoxan is often accompanied by debilitating "chemotherapy fatigue", prolonged periods of weakness and exercise intolerance which may persist even after recovery from hematologic and gastrointestinal toxicities of such agents.

Compounds, compositions, and methods of the invention are useful for treatment and prevention of side effects of cancer chemotherapy related to mitochondrial dysfunction. This use of pyrimidine nucleotide precursors for attenuation of cancer chemotherapy side effects is conceptually and biochemically distinct from toxicity reduction of cytotoxic anticancer pyrimidine analogs, which is mediated though biochemical competition at the level of nucleotide antimetabolites.

Example 5 illustrates the protective effect of oral triacetyluridine in protecting against taxol-induced neuropathy.

Furthermore, hepatic mitochondrial redox state is one contributor to appetite regulation. Cancer patients often display "early satiety", contributing to anorexia, weight loss, and cachexia. Energy metabolism is often seriously disrupted in cancer patients, with energy-wasting futile cycles of hyperactive tumor glycolysis producing circulating lactate, which is converted by the liver back to glucose. Chemotherapy-induced mitochondrial injury further contributes to metabolic disruption.

As indicated in Example 2, treatment with a compound of the invention resulted in improved appetite in a patient with mitochondrial disease.

Mitochondria and Ovarian Function

A crucial function of the ovary is to maintain integrity of the mitochondrial genome in oocytes, since mitochondria passed on to a fetus are all derived from those present in oocytes at the time of conception. Deletions in mitochondrial DNA become detectable around the age of menopause, and are also associated with abnormal menstrual cycles. Since cells cannot directly detect and respond to defects in mitochondrial DNA, but can only detect secondary effects that affect the cytoplasm, like impaired respiration, redox status, or deficits in pyrimidine synthesis, such products of mitochondrial function participate as a signal for oocyte selection and follicular atresia, ultimately triggering menopause when maintenance of mitochondrial genomic fidelity and functional activity can no longer be guaranteed. This is analogous to apoptosis in cells with DNA damage, which undergo an active process of cellular suicide when genomic fidelity can no longer be achieved by repair processes. Women with mitochondrial cytopathies affecting the gonads often undergo premature menopause or display primary cycling abnormalities. Cytotoxic cancer chemotherapy often induces premature menopause, with a consequent increased risk of osteoporosis. Chemotherapy-induced amenorrhea is generally due to primary ovarian failure. The incidence of chemotherapy-induced amenorrhea increases as a function of age in premenopausal women receiving chemotherapy, pointing toward mitochondrial involvement. Inhibitors of mitochondrial respiration or protein synthesis inhibit hormone-induced ovulation, and furthermore inhibit production of ovarian steroid hormones in response to pituitary gonadotropins. Women with Downs syndrome typically undergo menopause prematurely, and also are subject to early onset of Alzheimer-like dementia. Low activity of cytochrome oxidase is consistently found in tissues of Downs patients and in late-onset Alzheimer's Disease.

Appropriate support of mitochondrial function or compensation for mitochondrial dysfunction therefore is useful for protecting against age-related or chemotherapy-induced menopause or irregularities of menstrual cycling or ovulation. Compounds and compositions of the invention, including also antioxidants and mitochondrial cofactors, are useful for treating and preventing amenorrhea, irregular ovulation, menopause, or secondary consequences of menopause.

In Example 1, treatment with a compound of the invention resulted in shortening of the menstrual cycle. Since the patient was in a persistent luteal phase, her response indicates that the administered pyrimidine nucleotide precursor reversed hyporesponsiveness to pituitary gonadotropins, which were presumably elevated to compensate for the ovarian hyporesponsiveness of mitochondrial origin.

Diagnosis of Mitochondrial Disease

The striking response of patients with mitochondrial disease to administration of compounds of the invention indicates that a clinical response to a pyrimidine nucleotide precursor administered according to the methods of the subject invention has diagnostic utility to detect possible mitochondrial disease. Molecular diagnosis of molecular lesions underlying mitochondrial dysfunction is difficult and costly, especially when the defect is not one of the more common mutations or deletions of mitochondrial DNA. Since the compounds and compositions of the invention are very safe when administered in accord with the methods of the subject invention, therapeutic challenge with a pyrimidine nucleotide precursor is an important diagnostic probe for suspected mitochondrial disease, especially when used in conjunction with tests for various aspects of mitochondrial dysfunction.

E. Administration and Formulation of Compounds and Compositions of the Invention In the case of all of the specific therapeutic targets for pyrimidine nucleotide precursor therapy of mitochondrial disease, compounds of the invention are typically administered one to three times per day. Acyl derivatives of uridine and cytidine are administered orally in doses of 0.01 to 0.5 grams per kilogram of body weight per day, with variations within this range depending on the amount required for optimal clinical benefit. Generally, optimum doses are between 0.05 and 0.3 grams/kg/day, divided into two or three separate doses taken 6 to 12 hours apart.

In the case of patients unable to receive oral medications, compounds of the invention, especially uridine, cytidine, and orotate esters can be administered, as required, by prolonged intravenous infusion, delivering daily doses of 0.01 to 0.5 grams/kg/day.

The pharmacologically active compounds optionally are combined with suitable pharmaceutically acceptable carriers comprising excipients and auxiliaries which facilitate processing of the active compounds. These are administered as tablets, suspensions, solutions, dragees, capsules, or suppositories. The compositions are administered for example orally, rectally, vaginally, or released through the buccal pouch of the mouth, and may be applied in solution form by injection, orally or by topical administration. The compositions may contain from about 0.1 to 99 percent, preferably from about 50 to 90 percent of the active compound(s), together with the excipient(s).

For parenteral administration by injection or intravenous infusion, the active compounds are suspended or dissolved in aqueous medium such as sterile water or saline solution. Injectable solutions or suspensions optionally contain a surfactant agent such as polyoxyethylenesorbitan esters, sorbitan esters, polyoxyethylene ethers, or solubilizing agents like propylene glycol or ethanol. The solution typically contains 0.01 to 5% of the active compounds.

Suitable excipients include fillers such as sugars, for example lactose, sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch or potato starch, gelatin, tragacanth, methyl cellulose, hydroxypropylmethyl cellulose, sodium carboxymethyl cellulose and/or polyvinyl pyrrolidone.

Auxiliaries include flow-regulating agents and lubricants, for example, silica, talc, stearic acid or salts thereof, such as magnesium stearate or calcium stearate and/or polyethylene glycol. Dragee cores are provided with suitable coatings which, if desired, are resistant to gastric juices. For this purpose, concentrated sugar solutions are used, which optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate are used. Dyestuffs or pigments are optionally added to the tablets or dragee coatings, for example, for identification or in order to characterize different compound doses.

The pharmaceutical preparations of the present invention are manufactured in a manner which is itself known, for example, by means of conventional mixing, granulating, dragee-making, dissolving, or lyophilizing processes. Thus, pharmaceutical preparations for oral use are obtained by combining the active compound(s) with solid excipients, optionally grinding the resulting mixture and processing the mixture of granules, after adding suitable auxiliaries, if desired or necessary, to obtain tablets or dragee cores.

Other pharmaceutical preparations which are useful for oral delivery include push-fit capsules made of gelatin, as well as soft-sealed capsules made of gelatin and a plasticizer such as glycerol or sorbitol. The push-fit capsules contain the active compound(s) in the form of granules which optionally are mixed with fillers such as lactose, binders such as starches and/or lubricants such as talc or magnesium stearate, and, optionally stabilizers. In soft capsules, the active compounds are preferably dissolved or suspended in suitable liquids such as fatty oils, liquid paraffin, or polyethylene glycols. In addition, stabilizers optionally are added.

Pharmaceutical preparations which are used rectally include, for example, suppositories which consist of a combination of active compounds with a suppository base. Suitable suppository bases are, for example, natural or synthetic triglycerides, paraffin hydrocarbons, polyethylene glycols or higher alkanols. In addition, gelatin rectal capsules which consist of a combination of the active compounds with a base are useful. Base materials include, for example, liquid triglycerides, polyethylene glycols, or paraffin hydrocarbons. In another embodiment of the invention, an enema formulation is used, which optionally contains viscosity-increasing excipients like methylcellulose, hydroxypropylmethylcellulose, carboxymethycellulose, carbopol, glycerine polyacrylates, or other hydrogels.

Suitable formulations for parenteral administration include aqueous solutions of the active compounds in water soluble form, for example, water soluble salts.

In addition, suspensions of the active compounds as appropriate in oily injection suspensions are administered. Suitable lipophilic solvents or vehicles include fatty oils, for example, sesame oil, or synthetic fatty acid esters, for example, ethyl oleate or triglycerides. Aqueous injection suspensions optionally include substances which increase the viscosity of the suspension which include, for example, sodium carboxymethylcellulose, sorbitol and/or dextran. The suspension optionally contains stabilizers.

F. Synthesis of the Compounds of the Invention

Acyl derivatives of cytidine and uridine are synthesized typically by acylation methods involving reaction of acid chlorides or acid anhydrides with cytidine or uridine.

The synthesis of 2',3',5'-tri-O-pyruvyluridine is shown in Example 6.

The following examples are illustrative, but not limiting of the methods and compositions of the present invention. Other suitable modifications and adaptations of a variety of conditions and parameters normally encountered in clinical therapy which are obvious to those skilled in the art are within the spirit and scope of this invention.

EXAMPLES

Example 1

Treatment of a Multisystem Mitochondrial Disorder with Triacetyluridine

A 29 year old woman with a partial Complex I deficiency, and whose son was diagnosed with mitochondrial disease leading to stroke-like episodes, ataxia, and encephalopathy, presented with a multisystem mitochondrial disorder. Signs and symptoms included hemiplegic/aphasic migraines, grand-mal seizures, neurogenic bowel and bladder dysfunction, requiring catheterization approximately four times per day, dysphagia, autonomic and peripheral polyneuropathy producing painful paresthesias, tachycardia/bradycardia syndrome, and poor functional capacity with inability to climb a flight of stairs without stopping to rest, and declining cognitive performance with episodes of clouded sensorium and poor memory lasting hours to days.

After beginning treatment with 0.05 mg/kg/day of oral triacetyluridine, and for a duration of at least 6 months, this patient has not had seizures or migraines; her paresthesias related to peripheral neuropathy have resolved. She is able to void spontaneously on most days, requiring catheterization only once or twice per week. After 6 weeks of treatment with triacetyluridine, this patient was able to walk a full mile, which she has been unable to do for the past two years because of inadequate functional capacity. Her episodes of bradycardia during sleep and tachycardia during exertion have reduced in frequency; prior to treatment, tachycardia with a heart rate greater than 140 bpm occurred upon simple rise to stand, and after 6 weeks of triacetyluridine, tachycardia occurred only on hills and stairs. Her sensorium has cleared and memory deficits have improved markedly.

During treatment, this patients' menstrual cycles shortened from 4 weeks to two weeks, and she displayed a persistent luteal phase as evaluated by estradiol, progesterone, FSH and LH measurements. After several months, her cycle normalized to 4 weeks.

This patient demonstrates important features of the subject invention, in that 1) the compound of the invention caused improvements in virtually all features of a complex multisystem disease related to mitochondrial dysfunction in a variety of tissues, and that 2) compounds of the invention are unexpectedly useful for treating disease conditions related to a partial Complex I deficiency, which affects a portion of the mitochondrial respiratory chain that is outside of the sequence of electron transfers directly involved in de novo pyrimidine biosynthesis.

The transient shortening of this patient's menstrual cycle is interpreted as an improvement of ovarian function caused by triacetyluridine in the face of excessive hormonal stimulation by which the neuroendocrine system was attempting to compensate for ovarian dysfunction. Feedback between the ovaries and the hypothalamus led to gradual normalization of cycle time.

Example 2

Treatment of Refractory Epilepsy

An 11 year old boy had refractory epilepsy since age 4.5, apparently due to a multiple mitochondrial DNA deletion syndrome. In December 1997, his condition deteriorated, including 2 admissions to an intensive care unit for crescendo epilepsy. Even with aggressive regimens of standard anticonvulsive therapy, this patient was having 8 to 10 grand-mal seizures per night, leaving him unable to attend school regularly or participate in sports activities. He also developed upper lip automaticity.

In the first three days after beginning treatment with oral triacetyluridine (initially at a dose of 0.05 g/kg/day, and incrementally increased to 0.1 and then 0.24 g/kg/day over the course of several weeks), there were no seizures, and involuntary lip movements ceased. There has subsequently been some recurrence of seizures especially during episodes of infection, though at a much lower frequency than prior to treatment with triacetyluridine. This patient has been able to return to school and resume active participation in sports. His appetite, cognitive function, and fine motor coordination have improved during therapy, resulting in improved academic performance and in outstanding performance in sports activities like baseball.

Example 3

Treatment of Renal Tubular Acidosis

A 2 year-old girl, with Leigh's Syndrome (subacute necrotizing encephalopathy) associated with severe Complex I deficiency, displayed renal tubular acidosis requiring intravenous administration of 25 mEq per day of sodium bicarbonate. Within several hours after beginning intragastric treatment with triacetyluridine at 0.1 g/mg/day, her renal tubular acidosis resolved and supplementary bicarbonate was no longer required to normalize blood pH. Triacetyluridine also resulted in rapid normalization of elevated circulating amino acid concentrations, and maintained lactic acid at low levels after withdrawal of dichloroacetate treatment, which was previously required to prevent lactic acidosis.

Example 4

Treatment of Developmental Delay

A 4.5 year-old girl with epilepsy, ataxia, language delay, and fat intolerance, and dicarboxylic aciduria was treated with triacetyluridine at a daily dose of 0.1 to 0.3 g/kg/day. Such treatment resulted in a 50% decline in seizure frequency, improvement of ataxia and motor coordination, restoration of dietary fat tolerance, and accelerated development of expressive language capabilities.

Example 5

Prevention of Taxol-induced Neuropathy

Peripheral neuropathy is a frequent, and often dose-limiting, side effect of important anticancer agents like cisplatin and taxol. In the case of taxol, sensory neuropathy occurs several days after administration. Taxol's mechanism of action involves stabilization of microtubules, which is useful for treating cancers, but is deleterious to peripheral neurons. Microtubule stabilization impairs axonal transport of cellular components. Mitochondria shuttle between the cell body and terminals of neurons, so that the expression of mitochondrial respiratory chain components can be regulated by nuclear transcription factors. During inhibition of mitochondrial shuttling, mitochondria distant from the nucleus undergo decline in expression of respiratory chain subunits encoded by the mitochondrial genome, due to inadequate exposure to mtDNA transcription factors, resulting in regional neuronal energy failure and other consequences of mitochondrial dysfunction.

Two groups of 10 mice each were treated with taxol, 21.6 mg/kg/day for 6 consecutive days by intraperitoneal injection. An additional group of 10 mice received injections of vehicle alone. One of the groups of taxol-treated mice received oral triacetyluridine, 4000 mg/kg b.i.d. Nine days after the initiation of taxol treatments, nociceptive sensory deficits were tested by determining tail-flick latency after exposure of the tip of the tail to focused thermal radiation with an infrared heat lamp. In this system, delays in the tail-flick response to radiant heat correlate with sensory nerve deficits.

| Group: | Tail flick latency |
|---|---|
| Control (no taxol) | 10.8 ± 0.5 seconds |
| Taxol | 16.0 ± 3.1 seconds |
| Taxol + triacetyluridine | 11.9 ± 0.7 seconds |

Taxol treatment impaired responses to painful stimuli as an index of toxic sensory neuropathy. Oral triacetyluridine treatment significantly attenuated taxol-induced alterations in tail-flick latency.

Example 6

Synthesis of Uridine Pyruvate

A. The preparation of pyruvyl chloride was accomplished by the reaction of alpha, alpha-dichloromethyl methyl ether and pyruvic acid using the procedure of Ottenheum and Man (Synthesis, 1975, p. 163).

B. Uridine (3.0 g, 12 mmol) was dried by toluene azeotrope under vacuum (3×), and then dissolved in DMF (20 mL) and pyridine (20 mL). The resultant solution was cooled to −10 degrees C. and 6.0 mL of pyruvyl chloride (produced in step A above) was added dropwise. The reaction mixture was stirred at room temperature under argon for 24 hours. Analysis by TLC (5% MeOH/$CH_2Cl_2$) showed the consumption of uridine. The reaction mixture was evaporated to dryness and partitioned between $CH_2Cl_2$ and aqueous sodium bicarbonate. The organic layer was washed with water, aqueous HCl (pH 3.0), and water; dried over sodium sulfate; concentrated; and purified using flash chromatography (silica gel, 5% MeOH/$C_2Cl_2$) to yield 1.4 g of uridine pyruvate, or 2',3',5'-tri-O-pyruvyluridine.

While the present invention has been described in terms of preferred embodiments, it is understood that variations and modifications will occur to those skilled in the art. Therefore, it is intended that the appended claims cover all such equivalent variations and modifications which come within the scope of the invention as claimed.

The invention claimed is:

1. A method for reducing side effects of cytotoxic cancer chemotherapy agents by administering a pyrimidine nucleotide precursor, where said cytotoxic cancer chemotherapy agent is not a pyrimidine nucleoside analog.

2. A method as in claim 1 wherein said side effects of cytotoxic cancer chemotherapy are selected from the group consisting of peripheral neuropathy, chemotherapy-induced menopause, chemotherapy-associated fatigue, and depressed appetite.

3. A method as in claim 1 wherein said pyrimidine nucleotide precursor is 2',3',5'-tri-O-acetyluridine.

4. A method as in claim 1 wherein said cytotoxic cancer chemotherapy agent is taxol.

* * * * *